US012606728B2

(12) United States Patent
Kopkalli et al.

(10) Patent No.: US 12,606,728 B2
(45) Date of Patent: Apr. 21, 2026

---

(54) AZEOTROPE OR AZEOTROPE-LIKE COMPOSITIONS OF 2-CHLORO-1,1,1,2-TETRAFLUOROPROPANE (HCFC-244bb) AND WATER

(71) Applicant: Honeywell International Inc., Charlotte, NC (US)

(72) Inventors: Haluk Kopkalli, Staten Island, NY (US); Daniel C. Merkel, Orchard Park, NY (US); Hang T. Pham, Amherst, NY (US)

(73) Assignee: Solstice Advanced Materials US, Inc., Wilmington, DE (US)

( * ) Notice: Subject to any disclaimer, the term of this patent is extended or adjusted under 35 U.S.C. 154(b) by 1021 days.

(21) Appl. No.: 17/774,057

(22) PCT Filed: Nov. 5, 2020

(86) PCT No.: PCT/IB2020/020071
§ 371 (c)(1),
(2) Date: May 3, 2022

(87) PCT Pub. No.: WO2021/090071
PCT Pub. Date: May 14, 2021

(65) Prior Publication Data
US 2023/0002657 A1 Jan. 5, 2023

Related U.S. Application Data

(60) Provisional application No. 62/931,494, filed on Nov. 6, 2019.

(51) Int. Cl.
*C09K 5/04* (2006.01)
*C07C 17/25* (2006.01)

(52) U.S. Cl.
CPC .............. *C09K 5/044* (2013.01); *C07C 17/25* (2013.01); *C09K 5/048* (2013.01); *C09K 2205/126* (2013.01); *C09K 2205/32* (2013.01)

(58) Field of Classification Search
CPC .......... C09K 5/04; C09K 5/044; C09K 5/045; C09K 5/048; C09K 2205/10;
(Continued)

(56) References Cited

U.S. PATENT DOCUMENTS 8,618,340 B2 * 12/2013 Kopkalli ................. C07C 17/25
                                                570/135
8,697,922 B2 * 4/2014 Nappa .................... C07C 17/25
                                                570/155
(Continued)

FOREIGN PATENT DOCUMENTS

CN      101913989 A  * 12/2010
CN      101913989 B    6/2013
(Continued)

OTHER PUBLICATIONS

International Search Report and Written Opinion issued in PCT/IB2020/020071, dated Feb. 9, 2021, 9 pages.
(Continued)

*Primary Examiner* — Matthew R Diaz
(74) *Attorney, Agent, or Firm* — Faegre Drinker Biddle & Reath LLP

(57) ABSTRACT

Heterogenous azeotrope or azeotrope-like compositions comprising 2-chloro-1,1,1,2-tetrafluoropropane (HCFC-244bb) and water which may include from about 0.05 wt. % to about 92.01 wt. % 2-chloro-1,1,1,2-tetrafluoropropane (HCFC-244bb) and from about 7.99 wt. % to about 99.95 wt. % water and having a boiling point between about −13.5° C. and about 14.5° C. at a pressure of between about 12.5 psia and about 16.5 psia. The azeotrope or azeotrope-
(Continued)

like compositions may be used to separate impurities from 2-chloro-1,1,2-tetrafluoropropane (HCFC-244bb).

19 Claims, 1 Drawing Sheet

(58) Field of Classification Search
CPC .......... C09K 2205/124; C09K 2205/24; C09K 2205/32; C07C 17/23; C07C 17/25; C07C 17/35; C07C 17/354; C07C 17/357; C07C 17/38; C07C 17/383; C07C 17/395; B01D 3/14; B01D 3/143; B01D 3/36; B01D 11/04
See application file for complete search history.

(56) References Cited

U.S. PATENT DOCUMENTS

| | | | | |
|---|---|---|---|---|
| 10,125,066 | B1 * | 11/2018 | Jungong | ............... C07C 17/383 |
| 2007/0197842 | A1 * | 8/2007 | Mukhopadhyay | .... C07C 17/206 |
| | | | | 570/155 |
| 2009/0211988 | A1 | 8/2009 | Pham et al. | |
| 2009/0242832 | A1 | 10/2009 | Pham et al. | |
| 2011/0270000 | A1 * | 11/2011 | Bektesevic | ............ C07C 17/25 |
| | | | | 570/155 |
| 2011/0275724 | A1 | 11/2011 | Hulse et al. | |
| 2014/0284517 | A1 | 9/2014 | Hulse et al. | |
| 2015/0005536 | A1 | 1/2015 | Wang et al. | |
| 2018/0273449 | A1 * | 9/2018 | Sun | ......................... C07C 17/25 |

FOREIGN PATENT DOCUMENTS

| | | | | |
|---|---|---|---|---|
| CN | 104744210 | A | * | 7/2015 |
| CN | 105026349 | A | | 11/2015 |
| CN | 106631682 | A | * | 5/2017 ........... C07C 17/383 |
| EP | 2970057 | B1 | | 11/2018 |

OTHER PUBLICATIONS

Extended European Search Report issued in EP Application 20886003.1, mailed Nov. 9, 2023, 9 pages.

* cited by examiner

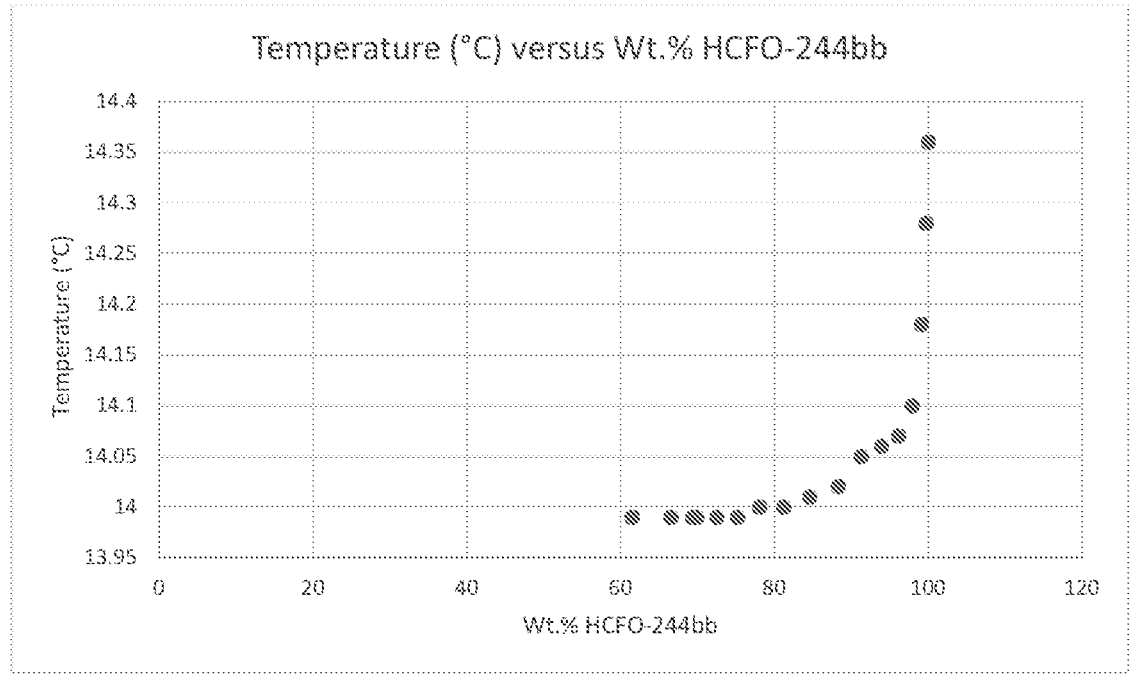

AZEOTROPE OR AZEOTROPE-LIKE COMPOSITIONS OF 2-CHLORO-1,1,1,2-TETRAFLUOROPROPANE (HCFC-244bb) AND WATER

CROSS-REFERENCE TO RELATED APPLICATION

This application is a U.S. National Stage application of International Application No. PCT/IB2020/020071 with an International filing date of 5 Nov. 2020, which claims priority to U.S. Provisional Application No. 62/931,494, filed Nov. 6, 2019, both of which are herein incorporated by reference in their entireties.

FIELD

The present disclosure pertains to azeotrope or azeotrope-like compositions and, in particular, azeotrope or azeotrope-like compositions comprising effective amounts of 2-chloro-1,1,1,2-tetrafluoropropane (HCFC-244bb) and water.

BACKGROUND OF THE DISCLOSURE

Hydrofluoroolefins (HFOs), such as tetrafluoropropenes, including 2,3,3,3-tetrafluoropropene (HFO-1234yf), are known to be effective refrigerants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

One manufacturing process for HFO-1234yf uses 1,1,2,3-tetrachloropropene (HCFC-1230xa) as starting raw material. The process comprises the following three steps:

Step (1) 1230xa+3HF→2-chloro-3,3,3-trifluoropropene (1233xf)+3HCl in a vapor phase reactor charged with a solid catalyst;

Step (2) 1233xf+HF→2-chloro-1,1,1,2-tetrafluoropropane (244bb) in a liquid phase reactor charged with a liquid catalyst; and Step (3) 244bb→1234yf+HCl in the liquid phase or in a vapor phase reactor.

During the foregoing process, by-products may be produced and/or impurities may be present. It is desirable to have all reactants and intermediate products in a pure a form as possible to limit unwanted side reactions. Therefore, methods of reducing impurities in reactants and intermediate products are desired.

SUMMARY

The present disclosure provides azeotrope or azeotrope-like compositions of 2-chloro-1,1,1,2-tetrafluoropropane (HCFC-244bb) and water.

It is well-recognized in the art that it is not possible to predict the formation of azeotropes, and the present inventors have discovered unexpectedly that 2-chloro-1,1,1,2-tetrafluoropropane (HCFC-244bb) and water form azeotrope or azeotrope-like compositions and, in particular, form heterogeneous azeotrope or azeotrope-like compositions.

The present disclosure provides a composition comprising an azeotrope or azeotrope-like composition consisting essentially of effective amounts of 2-chloro-1,1,1,2-tetrafluoropropane (HCFC-244bb) and water, wherein the azeotrope or azeotrope-like composition preferably has a boiling point between about 13.5° C. and about 14.5° C., preferably between about 13.99° C. and about 14.02° C., at a pressure of between about 12.5 psia and about 16.5 psia, preferably about 14.5 psia.

The azeotrope or azeotrope-like composition may consist essentially of from about 0.05 wt. % to about 92.01 wt. % 2-chloro-1,1,1,2-tetrafluoropropane (HCFC-244bb) and from about 7.99 wt. % to about 99.95 wt. % water. The azeotrope or azeotrope-like composition may consist essentially of from about 61 wt. % to about 90 wt. % 2-chloro-1,1,1,2-tetrafluoropropane (HCFC-244bb) and from about 10 wt. % to about 39 wt. % water; or from 61.39 wt. % to about 88.29 wt. % 2-chloro-1,1,1,2-tetrafluoropropane (HCFC-244bb) and from about 11.71 wt. % to about 38.61 wt. % water. The azeotrope or azeotrope-like composition preferably has a boiling point between about 13.5° C. and about 14.5° C., preferably between about 13.99° C. and about 14.02° C., at a pressure of between about 12.5 psia and about 16.5 psia, preferably about 14.5 psia.

The present disclosure also provides a method of forming an azeotrope or azeotrope-like composition comprising the step of combining 2-chloro-1,1,1,2-tetrafluoropropane (HCFC-244bb) and water to form an azeotrope or azeotrope-like composition consisting essentially of effective amounts of 2-chloro-1,1,1,2-tetrafluoropropane (HCFC-244bb) and water and having a boiling point between about 13.5° C. and about 14.5° C. at a pressure of between about 12.5 psia and about 16.5 psia.

The present disclosure further provides a method of separating impurities from a composition which includes 2-chloro-1,1,1,2-tetrafluoropropane (HCFC-244bb) and at least one impurity, comprising the steps of: providing a composition including 2-chloro-1,1,1,2-tetrafluoropropane (HCFC-244bb) and at least one impurity; modifying the relative amounts of 2-chloro-1,1,1,2-tetrafluoropropane (HCFC-244bb) and water, and subjecting the composition to conditions effective to form an azeotrope or azeotrope-like composition consisting essentially of, or consisting of, effective amounts of 2-chloro-1,1,1,2-tetrafluoropropane (HCFC-244bb) and water; and separating the azeotrope or azeotrope-like composition from the composition including 2-chloro-1,1,1,2-tetrafluoropropane (HCFC-244bb), wherein the separation step may comprise at least one of phase separation, distillation, and fractionation. In this context, 'impurity' (and 'impurities') covers substances that are intended to be separated from the 2-chloro-1,1,1,2-tetrafluoropropane (HCFC-244bb), although the substances to be separated can nevertheless have value themselves. An example of such an 'impurity' is 2,3,3,3-tetrafluoropropene (HFO-1234yf), which is a highly valuable commercial product that can be sold to generate revenue. The claims refer to 'other substances' instead of 'impurity' to emphasize this point, and the terms 'other substances' and 'impurity' are intended to be used interchangeably in the present disclosure in this context.

In the foregoing method, the step of modifying the relative amounts of 2-chloro-1,1,1,2-tetrafluoropropane (HCFC-244bb) and water may involve adding 2-chloro-1,1,1,2-tetrafluoropropane (HCFC-244bb) to the composition, adding water to the composition, or adding both 2-chloro-1,1,1,2-tetrafluoropropane (HCFC-244bb) and water to the composition.

The present disclosure also provides a method of producing 2,3,3,3-tetrafluoropropene (HFO-1234yf) comprising converting at least some of the 2-chloro-1,1,1,2-tetrafluoropropane (HCFC-244bb) present in the azeotrope or azeotrope-like composition defined above into 2,3,3,3-tetrafluoropropene (HFO-1234yf). This method covers both direct conversion (where HCFC-244bb is present in an azeotrope at the point it is converted into HFO-1234yf) and indirect conversion (e.g. where HCFC-244bb previously present in the azeotrope or azeotrope-like composition is not part of the azeotrope or azeotrope-like composition at the point it is converted into HFO-1234yf). The latter possibility includes, for example, converting HCFC-244bb into HFO-1234yf in a reaction mixture that does not comprise the azeotrope/azeotrope-like composition of the present disclosure because other substances present that disrupt the azeotropy, but wherein the molecules of HCFC-244bb had previously been in the form of the azeotrope/azeotrope-like composition. The method may involve reacting the HCFC-244bb with a base, wherein the base may be a caustic base, preferably an alkali metal hydroxide, preferably KOH or NaOH. The reaction may be conducted in an aqueous environment, preferably in the presence of a phase transfer catalyst, preferably an ammonium halide, preferably a trialkylammonium halide or a tetraalkylammonium halide, preferably a trialkylammonium chloride or a tetraalkylammonium chloride. Converting the 2-chloro-1,1,1,2-tetrafluoropropane (HCFC-244bb) into 2,3,3,3-tetrafluoropropene (HFO-1234yf) may preferably occur at a temperature of from about 0° C. to about 100° C., preferably from about 20° C. to about 90° C., preferably from about 50° C. to about 90° C., preferably from about 60° C. to about 80° C. Converting the 2-chloro-1,1,1,2-tetrafluoropropane (HCFC-244bb) into 2,3,3,3-tetrafluoropropene (HFO-1234yf) may suitably occur at super-atmospheric pressure, atmospheric pressure, or sub-atmospheric pressure.

DESCRIPTION OF THE DRAWING

FIG. 1 is a plot of boiling point versus percentage of 2-chloro-1,1,1,2-tetrafluoropropane (HCFC-244bb) in water.

DETAILED DESCRIPTION

In the first step (above), starting materials such as 1,1,2,3-tetrachloropropene ("HCO-1230xa" or "1230xa") and/or 1,1,1,2,3-pentachloropropane ("HCC-240db" or "240db") and/or 2,3,3,3-tetrachloropropane (HCO-1230xf) are reacted with anhydrous hydrogen fluoride (HF) in a first vapor phase reactor (fluorination reactor) to produce a mixture of at least HCFO-1233xf (2-chloro-3,3,3-trifluoropropene) and HCl. The reaction can be carried out at a temperature of about 200° C. to about 400° C. and a pressure of about 0 to about 200 psig. The effluent stream exiting the vapor phase reactor may optionally comprise additional components, such as un-reacted hydrogen fluoride (HF), heavy intermediates, 2-chloro-1,1,1,2-tetrafluoropropane (HCFC-244bb), 1,1,1,2,2-pentafluoropropane (HFC-245cb), and the like.

The reaction may be conducted in any reactor suitable for a vapor phase fluorination reaction. The reactor may be constructed from materials which are resistant to the corrosive effects of hydrogen fluoride and catalyst such as Hastelloy©, Inconel©, Monel©, and the like. In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures any of which may be optionally halogenated. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3/carbon$, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082, the contents of which are incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

In an embodiment, the molar ratio of hydrogen fluoride (HF) to a compound of Formula I, II or III in Step 1 reaction ranges from about 1:1 to about 50:1, in one embodiment; from about 10:1 to about 50:1, in another embodiment; and in a further embodiment, from about 10:1 to about 20:1. In an embodiment, the reaction between HF and the compound of I, II or III is carried out at a temperature from about 200° C. to about 600° C.; in another embodiment, from about 200° C. to about 400° C.; in another embodiment, from about 200° C. to about 300° C. The reaction pressure, in an embodiment, ranges from about 0 psig to about 500 psig; in another embodiment, from about 20 psig to about 200 psig, and in a further embodiment, from about 50 to about 100 psig.

For example, when the compound of Formula I is 1230xa, the molar ratio of HF to 1230xa in Step 1 of the reaction ranges from about 1:1 to about 50:1 in one embodiment; from about 10:1 to about 50:1, in another embodiment; and in a further embodiment, from about 10:1 to about 20:1. In an embodiment, the reaction between HF and 1230xa is carried out at a temperature from about 200° C. to about 600° C.; in another embodiment, from about 200° C. to about 400° C.; in another embodiment, from about 200° C. to about 300° C. The reaction pressure, in an embodiment, ranges from about 0 psig to about 500 psig; in another embodiment, from about 20 psig to about 200 psig, and in a further embodiment, from about 50 to about 100 psig.

Similarly, when the compound of Formula II is 2,3,3,3-tetrachloro-1-propene (HCC-1230xf or 1230xf), the molar ratio of HF to 1230xf in step 1 of the reaction, in one embodiment, ranges from about 1:1 to about 50:1; in another embodiment, from about 10:1 to about 50:1, and, in still further embodiment, from about 10:1 to about 20:1. In an embodiment, the reaction between HF and 1230xf is carried out at a temperature from about 200° C. to about 600° C.; in another embodiment, from about 200° C. to about 400° C.; and, in another embodiment, from about 200° C. to about 300° C. The reaction pressure, in an embodiment, ranges from about 0 psig to about 500 psig; in another embodiment, from about 20 psig to about 200 psig, and in another embodiment, from about 50 to about 100 psig.

Similarly, when the compound of Formula III is 1,1,1,2,3-pentachloropropane (HCC-240db or 240db), the molar ratio of HF to 240db in step 1 of the reaction ranges from about 1:1 to about 50:1; in another embodiment, from about 10:1 to about 50:1; and in another embodiment, from about 10:1 to about 20:1. The reaction between HF and 240db is carried out, in an embodiment, at a temperature from about 200° C. to about 600° C.; in another embodiment, from about 200° C. to about 400° C., and in another embodiment, from about 200° C. to about 300° C. The reaction pressure, in an embodiment, ranges from about 0 psig to about 500 psig; in another embodiment, from about 20 psig to about 200 psig; and in a further embodiment, from about 50 to about 100 psig.

The first step of the reaction is not necessarily limited to a vapor phase reaction, as described above, but may also be performed using a liquid phase reaction or a combination of liquid and vapor phases, such as that disclosed in U.S. Published Patent Application No. 20070197842, the contents of which are incorporated herein by reference. It is also contemplated that the reaction can be carried out batch wise, continuously, or a combination of these. For embodiments in which the reaction comprises a liquid phase reaction, the reaction can be catalytic or non-catalytic. Lewis acid catalysts, such as metal-halide catalysts, including antimony halides, tin halides, thallium halides, iron halides, and combinations of two or more of these, may be employed. In certain embodiments, metal chlorides and metal fluorides are employed, including, but not limited to, $SbCl_5$, $SbCl_3$, $SbF_5$, $SnCl_4$, $TiCl_4$, $FeCl_3$ and combinations of two or more of these.

The fluorination reaction may be carried out to attain a single- or multi-pass conversion of at least 1% or higher, 5% or higher, 10% or higher or about 20% or higher. In certain preferred embodiments of the present invention, the starting reagent is converted to 1233xf in a single pass, wherein the reaction conditions achieve a conversion amount greater than 75%; in an embodiment, greater than 85%; in another embodiment, greater than 95%; and in another embodiment, greater than 99%. To this end, the resulting effluent includes small or trace amounts of unreacted starting material or may be substantially free of such compounds.

The effluents from the fluorination reaction step, Step 1, including any intermediate effluents that may be present in multi-stage reactor arrangements, are processed to achieve desired degrees of separation. For example, in embodiments in which the reactor effluent includes 2-chloro-3,3,3-trifluoropropene (HCFO-1233xf), the effluent will generally also include HCl, unreacted HF, and trace amounts, if any, of unreacted starting component (e.g. 1230xa, 1230xf and/or 240db). The effluent may also include one or more byproduct organics such as underfluorinated and/or overfluorinated intermediates. Non-limiting examples of underfluorinated intermediates include trichlorofluoropropene (1231) isomers and 2,3-dichloro-3,3-difluoropropene (1232xf), and non-limiting examples of overfluorinated intermediates include 2-chloro-1,1,1,2-tetrafluoropropane (244bb) and 1,1,1,2,2-pentafluoropropane (245cb) and HFO-1234yf and combinations thereof. In further embodiments, the impurity is hydrogen fluoride. Other by-product organics may also include, but are not limited to, dichlorotrifluoropropane (243) isomers, and trichlorodifluoropropane (242) isomers, and dimers derived from one or more of the starting compounds. By way of non-limiting example, dimers derived from 1230xa include, but are not limited to, $C_6H_3F_6Cl$, $C_6H_3F_7Cl_2$, $C_6F_6Cl_2$, $C_6H_8C_2$, $C_6F_5Cl_3$, $C_6H_3F_2Cl_5$, and the like.

After HCl is removed by distillation and a portion of the HF is removed by phase separation, water is added to the remaining effluent from Step 1 in an effective amount to form an azeotrope or azeotrope-like mixture comprising 2-chloro-3,3,3-trifluoropropene (HCFO-1233xf) and water, which can then be separated from the effluent with its impurities by techniques described herein. The 2-chloro-3,3,3-trifluoropropene (HCFO-1233xf) is then separated from the water as described herein then is fed to the hydrofluorination reactor of Step 2, discussed below.

In Step 2 of the aforementioned process for forming 2,3,3,3-tetrafluoroprop-1-ene, the purified 2-chloro-3,3,3-trifluoropropene (HCFO-1233xf) is converted to 2-chloro-1,1,1,2-tetrafluoropropane (244bb). In one embodiment, this step may be performed in the liquid phase in a liquid phase reactor, which may be TFE or PFA-lined. Such a process may be performed in a temperature range of about 70° to about 120° C. and at a pressure ranging from about 50 to about 120 psig.

Any liquid phase fluorination catalyst may be used in the invention. A non-exhaustive list includes Lewis acids, transition metal halides, transition metal oxides, Group IVb metal halides, Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

The catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

Step 2 of the reaction, in which 244bb product is formed, is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the feed stream including 2-chloro-3,3,3-trifluoropropene (HCFO-1233xf) is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

The effluent from the hydrofluorination reaction step (Step 2), which consists mainly of 244bb and HF (plus small amounts of unreacted 2-chloro-3,3,3-trifluoropropene (HCFO-1233xf), overfluorinated by-product 245cb, HCl, and $Cl_2$), is processed to achieve desired degrees of separation and/or other processing. For example, the product stream is fed to a lights removal column where a stream consisting of mainly 245cb, HCl, and $Cl_2$ exits the top of the column and is sent to a thermal-oxidizer (T-OX) for destruction. In one embodiment, water is added to the lights removal column bottom stream consisting mainly of 244bb and HF (plus a small amount of unreacted 1233xf) to form an azeotrope or azeotrope-like mixture comprised of 1233xf and water. In one embodiment, 244bb is not present in this mixture, in which case the 1233xf is separated from the water by techniques known in the art, as described hereinabove, such as by distillation. In another embodiment, the 244bb is also present in the azeotrope or azeotrope-like mixture comprised of 1233xf and water. The 244bb is then separated from the 1233xf by techniques known in the art, such as described in U.S. Pat. No. 8,252,965, the contents of which are incorporated by reference. The 1233xf that is separated may be recycled back to the hydrofluoronation reactor of Step 2, as described above.

Step 3 of the process can be conducted in the vapor phase or liquid phase. When producing HFO-1234yf in the vapor phase, the 244bb is fed to a second vapor phase reactor (dehydrochlorination reactor) to be dehydrochlorinated to make the desired product 2,3,3,3-tetrafluoroprop-1-ene (1234yf). This reactor may optionally contain a catalyst that can catalytically dehydrochlorinate HCFC-244bb to make HFO-1234yf; however, in an embodiment, the reactor contains the catalyst.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metals halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

In one aspect, neutral metals, i.e., zero valent, metals, metal alloys and their mixtures, are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel® 400, Incoloy® 825, Inconel® 600, and Inconel® 625. Such catalysts may be provided as discrete supported or unsupported elements and/or as part of the reactor and/or the reactor walls.

Exemplary, but non-limiting, catalysts include activated carbon, stainless steel (e.g. SS 316), austenitic nickel-based alloys (e.g. Inconel® 625), nickel, fluorinated 10% CsCl/MgO, and 10% $CsCl/MgF_2$ and the like. In an embodiment, the reaction temperature ranges from about 300 to about 550° C., and the reaction pressure may range from about 0 to about 150 psig. The reactor effluent may be fed to a caustic scrubber or to a distillation column to remove the by-product of HCl to produce an acid-free organic product which, optionally, may undergo further purification using one or any combination of purification techniques that are known in the art.

Step 3 can also be conducted in the liquid phase. Converting 2-chloro-1,1,1,2-tetrafluoropropane (HCFC-244bb) into 2,3,3,3-tetrafluoropropene (HFO-1234yf) can, for example, be carried out by employing a base to dehydrochlorinate the 2-chloro-1,1,1,2-tetrafluoropropane (HCFC-244bb). The base can be a caustic base, preferably selected from the group consisting of an alkali metal hydroxide, an alkali metal oxide, an alkaline earth metal hydroxide, an alkaline earth metal oxide and combinations thereof. Preferable examples of the caustic base are KOH, NaOH, LiOH, $Mg(OH)_2$, $Ca(OH)_2$, CaO and combinations thereof. Caustic bases can be added to the reaction in solid form or in a solution. When provided in solution, it is preferable that the solvent is water or an alcohol, preferably MeOH or EtOH. KOH is especially preferred, and is preferably provided as an aqueous solution, preferably comprising from about 5% to about 62% by weight of KOH, preferably 5% to 55% by weight. The liquid phase dehydrochlorination is preferably conducted in an aqueous environment. In the context of a liquid phase step 3, an aqueous environment is one in which the liquid phase reaction mixture comprises 5-80 wt. % water, preferably 10-60 wt. % water, more preferably 20-40 wt. % water. It is also preferable to utilize a phase transfer catalyst, especially when conducting the reaction in an aqueous environment because it is believed to aid reactivity by encouraging intimate contact between the base and the 2-chloro-1,1,1,2-tetrafluoropropane (HCFC-244bb). Such phase transfer catalysts may include, but are not limited to, crown ethers (e.g. 18-crown-6), onium salts (e.g. phosphonium salts or ammonium salts with a halide anion), cryptands (e.g. $N[CH_2CH_2OCH_2CH_2OCH_2CH_2]_3N$), polyalkylene glycols (e.g. poly(ethylene glycol), derivatives thereof, and combinations thereof. In one embodiment, the phase transfer catalyst is Aliquat 336. Onium salts, especially ammonium salts, are preferred. The ammonium salt is preferably an ammonium halide, preferably a trialkylammonium halide or a tetraalkylammonium halide, preferably a trialkylammonium chloride or a tetraalkylammonium chloride.

The liquid phase version of step 3 is preferably conducted at a temperature of at a temperature of from about 0° C. to about 100° C., preferably from about 20° C. to about 90° C., preferably from about 50° C. to about 90° C., preferably from about 60° C. to about 80° C. Converting the 2-chloro-1,1,1,2-tetrafluoropropane (HCFC-244bb) into 2,3,3,3-tetrafluoropropene (HFO-1234yf) may suitably occur at superatmospheric pressure, atmospheric pressure, or subatmospheric pressure. These temperatures and pressures are especially useful when conducting step 3 in the liquid phase with a base, as described above.

WO-2011/139646 discloses further experimental details for converting 2-chloro-1,1,1,2-tetrafluoropropane (HCFC-244bb) into 2,3,3,3-tetrafluoropropene (HFO-1234yf) in the liquid phase, the contents of which are incorporated herein.

An alternative process to make HFO-1234yf employs 1,2-dichloro-3,3,3-trifluoropropane (HCFC-243db) as starting raw material and is conducted in the vapor and liquid phase. In this alternative, the process comprises the following three steps (where Steps (2) and (3) are identical to those above):

Step (1): 243db→1233xf+HCl in the vapor phase (with or without catalyst) or 243db+base→1233xf+$H_2O$ in the liquid phase (optionally with phase transfer catalyst, and/or solvent and/or salt).

Step (2): 1233xf+HF→244bb in a liquid phase reactor charged with a liquid hydrofluorination catalyst; and Step (3): 244bb→1234yf+HCl in a vapor phase reactor (with or without catalyst) or in the liquid phase.

In the alternative process, wherein the starting composition includes 243db, 243db is dehydrohalogenated to produce a product mixture containing 1233xf. The dehydrohalogenation reaction is a dehydrochlorination reaction when the starting composition comprises 243db. The dehydrochlorination reaction is performed in a reaction zone and may occur in the vapor phase with a catalyst or in liquid phase with base and optionally phase transfer catalyst, and/or solvent and/or salt. For example, WO 2012/115934 discloses vapor phase reaction of 243db with a carbon catalyst. WO 2012/115938 discloses vapor phase reaction of 243db with a chromium oxyfluoride catalyst. WO 2017/044719 discloses reaction of 243db with a fluorinated alkane in the presence of a fluorination catalyst to produce 1233xf, as well as other compounds useful for producing 1234yf. WO 2017/044724 discloses liquid phase reaction of 243db with caustic. If the dehydrochlorination reaction is performed in the vapor phase, HCl is produced, on the other hand, when the dehydrochlorination reaction is conducted in the liquid phase, no HCl is produced. Other methods may be used when starting with a compound having Formula (III) as will be known to those skilled in the art.

For embodiments where it is desired to maintain moisture- and impurity-free conditions during the synthesis of 1234yf, the reactants and intermediate products may be purified. For example, removing impurities from 2-chloro-3,3,3-trifluoropropene (HCFO-1233xf) is desirable.

It has been found that 2-chloro-1,1,1,2-tetrafluoropropane (HCFC-244bb) and water form heterogeneous azeotrope and azeotrope-like compositions or mixtures, and the present disclosure provides heterogenous azeotrope or azeotrope-like compositions comprising 2-chloro-1,1,1,2-tetrafluoropropane (HCFC-244bb) and water. The azeotrope or azeotrope-like compositions may consist essentially of 2-chloro-1,1,1,2-tetrafluoropropane (HCFC-244bb) and water, or the azeotrope or azeotrope-like compositions may consist of 2-chloro-1,1,1,2-tetrafluoropropane (HCFC-244bb) and water.

The present inventors have found experimentally that 2-chloro-1,1,1,2-tetrafluoropropane (HCFC-244bb) and water form an azeotrope or azeotrope-like composition.

A heterogenous azeotrope consists of two liquid phases and one vapor phase all in equilibrium. For a heterogenous azeotrope at a given temperature and pressure, the composition of each of the two liquid phases and the composition of the vapor phase remain constant. If a heterogenous azeotrope is formed, at a constant pressure the boiling point of the heterogenous azeotrope will be less than the lower boiling point component (a "minimum boiling azeotrope").

An "azeotrope" (or "azeotropic") composition is a unique combination of two or more components. An azeotrope can be either homogenous (which has one liquid phase) or heterogenous (which has two liquid phases). An azeotrope composition can be characterized in various ways. For example, at a given pressure, an azeotrope composition boils at a constant characteristic temperature which is either greater than the higher boiling point component (maximum boiling azeotrope) or less than the lower boiling point component (minimum boiling azeotrope). However, in the case of a heterogenous azeotrope the boiling point of the azeotrope will always be below the boiling point of the lower boiling point component. At this characteristic temperature a homogenous azeotrope has the same composition in both the vapor and liquid phases. In the case of a heterogenous azeotrope then at this characteristic temperature the composition of each of the two liquid phases and the vapor phase will remain constant upon boiling. The azeotrope composition does not fractionate upon boiling or evaporation. Therefore, the components of the azeotrope composition cannot be separated during a phase change.

A homogenous azeotrope composition is also characterized in that at the characteristic azeotrope temperature, the bubble point pressure of the liquid phase is identical to the dew point pressure of the vapor phase. The behavior of an azeotrope composition is in contrast with that of a non-azeotrope composition in which during boiling or evaporation, the liquid composition changes to a substantial degree.

One of ordinary skill in the art would understand however that at different pressures, both the composition and the boiling point of the azeotrope composition will vary to some extent. Therefore, depending on the temperature and/or pressure, an azeotrope composition can have a variable composition. The skilled person would therefore understand that composition ranges, rather than fixed compositions, can be used to define azeotrope compositions. In addition, an azeotrope may be defined in terms of exact weight percentages of each component of the compositions characterized by a fixed boiling point at a specified pressure.

An "azeotrope-like" composition is a composition of two or more components which behaves substantially as an azeotrope composition. Thus, for the purposes of this disclosure, an azeotrope-like composition is a combination of two or more different components which, in the case of a homogenous azeotrope when in liquid form under given pressure, will boil at a substantially constant temperature, and which will provide a vapor composition substantially identical to the liquid composition undergoing boiling. In the case of a heterogenous azeotrope two liquid phases form under a given pressure which will be covered by a vapor composition. Each of the two liquid phases and the vapor phase will remain substantially constant on boiling.

For the purposes of this disclosure, an azeotrope-like composition is a composition or range of compositions which boil(s) at a temperature range of between about 12.0° C. and 13.6° C. at a pressure from about 12.5 psia to about 16.5 psia.

Azeotrope or azeotrope-like compositions can be identified using a number of different methods.

For the purposes of this disclosure the azeotrope or azeotrope-like composition is identified experimentally using an ebulliometer (Walas, Phase Equilibria in Chemical Engineering, Butterworth-Heinemann, 1985, 533-544). An ebulliometer is designed to provide extremely accurate measurements of the boiling points of liquids by measuring the temperature of the vapor-liquid equilibrium.

The boiling points of each of the components alone are measured at a constant pressure. As the skilled person will appreciate, for a binary azeotrope or azeotrope-like composition, the boiling point of one of the components of the composition is initially measured. The second component of the composition is then added in varying amounts and the boiling point of each of the obtained compositions is measured using the ebulliometer at said constant pressure. In the case of a ternary azeotrope the initial composition would comprise of a binary blend and a third component is added in varying amounts. The boiling point of each of the obtained ternary compositions is measured using the ebulliometer at said constant pressure.

The measured boiling points are plotted against the composition of the tested composition, for example, for a binary azeotrope, the amount of the second component added to the composition, (expressed as either weight % or mole %). The presence of an azeotrope composition can be identified by the observation of a maximum or minimum boiling temperature which is greater or less than the boiling points of any of the components alone.

As the skilled person will appreciate, the identification of the azeotrope or azeotrope-like composition is made by the comparison of the change in the boiling point of the composition on addition of the second component to the first component, relative to the boiling point of the first component. Thus, it is not necessary that the system be calibrated to the reported boiling point of the particular components in order to measure the change in boiling point.

As previously discussed, at the maximum or minimum boiling point, the composition of the vapor phase will be identical to the composition of the liquid phases. The azeotrope-like composition is therefore that composition of components which provides a substantially constant minimum or maximum boiling point, that is a boiling point between about 13.5° C. and about 14.5° C. at a pressure of between about 12.5 psia and about 16.5 psia at which substantially constant boiling point the composition of the vapor phase will be substantially identical to the composition of the liquid phases.

The present disclosure provides an azeotrope or azeotrope-like composition which comprises effective amounts of 2-chloro-1,1,1,2-tetrafluoropropane (HCFC-244bb) and water to form an azeotrope or azeotrope-like composition. As used herein, the term "effective amount" is an amount of each component which, when combined with the other component, results in the formation of an azeotrope or azeotrope-like composition.

The present azeotrope or azeotrope-like compositions may consist essentially of combinations of 2-chloro-1,1,1, 2-tetrafluoropropane (HCFC-244bb) and water or consist of combinations of 2-chloro-1,1,1,2-tetrafluoropropane (HCFC-244bb) and water.

As used herein, the term "consisting essentially of", with respect to the components of an azeotrope or azeotrope-like composition or mixture, means the composition contains the indicated components in an azeotrope or azeotrope-like ratio, and may contain additional components provided that the additional components do not form new azeotrope or azeotrope-like systems. For example, azeotrope mixtures consisting essentially of two compounds are those that form binary azeotropes, which optionally may include one or more additional components, provided that the additional components do not render the mixture non-azeotropic and do not form an azeotrope with either or both of the compounds (e.g., do not form a ternary or higher azeotrope).

The present disclosure also provides a method of forming an azeotrope or azeotrope-like composition by mixing, combining, or blending, effective amounts of 2-chloro-1,1, 1,2-tetrafluoropropane (HCFC-244bb) and water. Any of a wide variety of methods known in the art for combining two or more components to form a composition can be used in the present methods. For example, 2-chloro-1,1,1,2-tetrafluoropropane (HCFC-244bb) and water can be mixed, blended, or otherwise combined by hand and/or by machine, as part of a batch or continuous reaction and/or process, or via combinations of two or more such steps. The components can be provided in the required amounts, for example by weighing and then combining the amounts.

The azeotrope or azeotrope-like composition may have a boiling point between about 13.5° C. and about 14.5° C. at a pressure of between about 12.5 psia and about 16.5 psia, and consists essentially of, or consists of, from about 0.05 wt. % to about 92.01 wt. % 2-chloro-1,1,1,2-tetrafluoropropane (HCFC-244bb) and from about 7.99 wt. % to about 99.95 wt. % water.

The present disclosure also provides a composition comprising the azeotrope or azeotrope-like composition. For example, there is provided a composition comprising at least about 14 wt. % of the azeotrope or azeotrope-like compositions, or at least about 21 wt. % of the azeotrope or azeotrope-like compositions, or at least about 25 wt. % of the azeotrope or azeotrope-like compositions, or at least about 70 wt. % of the azeotrope or azeotrope-like compositions, or at least about 90 wt. % of the azeotrope or azeotrope-like compositions, or at least 95 wt. % of the azeotrope or azeotrope-like compositions, or at least 99 wt. % of the azeotrope or azeotrope-like compositions.

The azeotrope or azeotrope-like composition comprising, consisting essentially of, or consisting of effective amounts of 2-chloro-1,1,1,2-tetrafluoropropane (HCFC-244bb) and water disclosed herein may be used for separating impurities from 2-chloro-1,1,1,2-tetrafluoropropane (HCFC-244bb).

The preparation of azeotropic or azeotrope-like compositions comprising, consisting essentially of, or consisting of effective amounts of 2-chloro-1,1,1,2-tetrafluoropropane (HCFC-244bb) and water allows separation techniques such as azeotropic distillation, for example, to be used to remove impurities from 2-chloro-1,1,1,2-tetrafluoropropane (HCFC-244bb).

In particular, an azeotrope or azeotrope-like composition comprising, consisting essentially of, or consisting of effective amounts of 2-chloro-1,1,1,2-tetrafluoropropane (HCFC-244bb) and water may be formed from a composition including 2-chloro-1,1,1,2-tetrafluoropropane (HCFC-244bb), water, and at least one impurity. Following the formation of the azeotrope or azeotrope-like composition, the azeotrope or azeotrope-like composition may be separated from the other chemical compounds by a suitable method, such as by distillation, phase separation, or fractionation.

In one example, the present disclosure provides a method of separating impurities from 2-chloro-1,1,1,2-tetrafluoropropane (HCFC-244bb), comprising the steps of providing a primary composition of crude 2-chloro-1,1,1,2-tetrafluoropropane (HCFC-244bb), modifying the relative amounts of 2-chloro-1,1,1,2-tetrafluoropropane (HCFC-244bb) and water, and subjecting the primary composition to conditions effective to form a secondary composition which is an azeotrope or azeotrope-like composition consisting essentially of, or consisting of, effective amounts of 2-chloro-1, 1,1,2-tetrafluoropropane (HCFC-244bb) and water, and separating the secondary composition from the primary composition by a separation technique such as phase separation, distillation, or fractionation, for example. Thereafter, the secondary composition may be subjected to further separation or purification steps to obtain purified 2-chloro-1,1,1,2-tetrafluoropropane (HCFC-244bb). The step of modifying the relative amounts of 2-chloro-1,1,1,2-tetrafluoropropane (HCFC-244bb) and water may involve adding 2-chloro-1,1,1,2-tetrafluoropropane (HCFC-244bb) to the composition, adding water to the composition, or adding both 2-chloro-1,1,1,2-tetrafluoropropane (HCFC-244bb) and water to the composition.

The azeotrope or azeotrope-like composition comprising, consisting essentially of, or consisting of effective amounts of 2-chloro-1,1,1,2-tetrafluoropropane (HCFC-244bb) and water can be used in the production of 2,3,3,3-tetrafluoropropene (HFO-1234yf). For example, the azeotrope or azeotrope-like composition can be combined with further components, such as a base and/or a phase transfer catalyst, to facilitate dehydrochlorinating the 2-chloro-1,1,1,2-tetrafluoropropane (HCFC-244bb) to form 2,3,3,3-tetrafluoropropene (HFO-1234yf). Residual 2-chloro-1,1,1,2-tetrafluoropropane (HCFC-244bb) present in crude 2,3,3,3-tetrafluoropropene HFO-1234yf) can be removed along with water in the form of the azeotrope or azeotrope-like composition of the present disclosure, wherein the removal can for example take the form of a distillation, phase separation or combination thereof. The azeotrope or azeotrope-like composition removed from the crude product can be recycled back to step 3, especially when conducting step 3 in the liquid phase.

It is also possible, though not inevitable, for the azeotrope or azeotrope-like composition to form in a reaction that produces 2,3,3,3-tetrafluoropropene (HFO-1234yf) from 2-chloro-1,1,2-tetrafluoropropane (HCFC-244bb). The existence of the azeotrope or azeotrope-like composition will depend on factors such as whether the azeotropy is disrupted by other substances present. Examples of how it is possible, though not inevitable, for the azeotrope or azeotrope-like composition to form include the following:

When water is present in the reaction as a solvent, e.g. when the reaction is conducted in an aqueous environment, such as when a base is used in an aqueous solution.

When water is evolved in a reaction. For example, dehydrochlorinating HCFC-244bb with hydroxide ions, in the presence or absence of water as a solvent, would evolve water molecules according to the following equation: $CF_3CFClCCH_3 + ^-OH \rightarrow CF_3CF=CH_2 + Cl^- + H_2O$. The skilled person will appreciate that it is possible for water molecules to be evolved when other types of base, especially caustic bases, are used.

The following non-limiting examples serve to illustrate the invention.

EXAMPLES

Example 1—Vapor Liquid Equilibrium (VLE) Study

An ebulliometer consisting of vacuum-jacketed tube with a dry-ice cooled condenser on top was further equipped with a Quartz Thermometer. The ebulliometer was initially charged with 16.21 grams of 2-chloro-1,1,2-tetrafluoropropane (HCFC-244bb). Water was then added incrementally and the boiling point temperature of the mixture was recorded. The results are depicted in Table 1 and shown graphically in FIG. 1.

TABLE 1

| Wt. % HCFC-244bb | Wt. % Water | Temperature (° C.) |
| --- | --- | --- |
| 100.00 | 0.00 | 14.36 |
| 99.69 | 0.31 | 14.28 |
| 99.08 | 0.92 | 14.18 |
| 97.89 | 2.11 | 14.10 |
| 96.14 | 3.86 | 14.07 |
| 93.92 | 6.08 | 14.06 |
| 91.27 | 8.73 | 14.05 |
| 88.29 | 11.71 | 14.02 |
| 84.60 | 15.40 | 14.01 |
| 81.21 | 18.79 | 14.00 |
| 78.08 | 21.92 | 14.00 |
| 75.19 | 24.81 | 13.99 |
| 72.50 | 27.50 | 13.99 |
| 69.39 | 30.61 | 13.99 |
| 66.54 | 33.46 | 13.99 |
| 69.92 | 36.08 | 13.99 |
| 61.49 | 38.51 | 13.99 |

As shown, the boiling point temperature of the mixture reached a minimum value and then flattened indicating the formation of a heterogeneous azeotrope. More specifically, the composition comprising about 61% to about 99% by weight of 2-chloro-1,1,2-tetrafluoropropane (HCFC-244bb) had a change in boiling point of less than 0.2° C. In addition, the composition comprising about 66% to about 99% by weight 2-chloro-1,1,2-tetrafluoropropane (HCFC-244bb) had a change in boiling point of less than 0.1° C. The ambient pressure during the measurements was 14.49 psia.

Example 2—Vapor-Liquid-Liquid Equilibrium (VLLE) Measurements

A 50:50 by weight mixture of 2-chloro-1,1,2-tetrafluoropropane (HCFC-244bb) and water was made in a Teflon cell at 23° C. Two separate phases were observed in the cell indicating that a heterogeneous azeotrope had been formed. The upper (water-rich) and lower (2-chloro-1,1,2-tetrafluoropropane (HCFC-244bb)-rich) phases were separated and analyzed. The compositions of the two phases is shown in Table 2, below.

TABLE 2

| Component | Upper Phase Wt. % | Lower Phase Wt. % |
| --- | --- | --- |
| HCFC-244bb | 0.05% | 92.01% |
| Water | 99.95% | 7.99% |

Example 3—Purification of 2-chloro-1,1,2-tetrafluoropropane (HCFC-244bb)

In this Example, a composition is provided which includes 2-chloro-1,1,2-tetrafluoropropane (HCFC-244bb) and an impurity, which may be HF. An effective amount of water is added to the composition, and the composition is subjected to conditions effective to form an azeotrope or azeotrope-like composition consisting essentially of, or consisting of, effective amounts of 2-chloro-1,1,2-tetrafluoropropane (HCFC-244bb) and water. Then, the azeotrope or azeotrope-like composition is separated from the composition including the primary compound by a separation technique such as phase separation, distillation, and/or fractionation.

Example 4—Separation of hydrogen fluoride (HF) from 2-chloro-1,1,1-tetrafluoropropane (HCFC-244bb)

In this Example, a composition is provided which includes a primary compound, 2-chloro-1,1,2-tetrafluoropropane (HCFC-244bb), together with hydrogen fluoride (HF) as an impurity. An effective amount of water is added to the composition, and the composition is subjected to conditions effective to form an azeotrope or azeotrope-like composition consisting essentially of, or consisting of, effective amounts of 2-chloro-1,1,2-tetrafluoropropane (HCFC-244bb) and water. Then, the azeotrope or azeotrope-like composition is separated from the composition including the primary compound by a separation technique such as phase separation, distillation, and/or fractionation.

Example 5—Separation of hydrogen fluoride (HF) from 2-chloro-1,1,1-tetrafluoropropane (HCFC-244bb)

In this Example, a composition is provided which includes a primary compound, such as 2-chloro-1,1,2-tetrafluoropropane (HCFC-244bb) together with hydrogen fluoride (HF) as an impurity. An effective amount of 2-chloro-1,1,2-tetrafluoropropane (HCFC-244bb) is added to the composition, and the composition is subjected to conditions effective to form an azeotrope or azeotrope-like composition consisting essentially of, or consisting of, effective amounts of 2-chloro-1,1,1,2-tetrafluoropropane (HCFC-244bb) and water. Then, the azeotrope or azeotrope-like composition is separated from the composition including the primary compound by a separation technique such as phase separation, distillation, and/or fractionation.

Example 6—Representative Procedure for Converting 2-chloro-1,1,1,2-tetrafluoropropane (HCFC-244bb) into 2,3,3,3-tetrafluoropropene (HFO-1234yf)

The dehydrochlorination of HCFC-244bb was carried out in one liter Parr reactor equipped with thermocouple and magnetic stirrer. 15 g Aliquat 336™ was added to reactor. Reactor was then closed and pressure tested. Afterwards 294 g of Organic mixture and 270 g of 45% KOH were added into reactor. The analysis of organic mixture using Gas Chromatography (GC) revealed 8.1 GC Area % of 1234yf, 89.5 GC Area % of 244bb, and 1.8 GC Area % of 1233xf. The stirrer was then turned on and the reactor was heated to 55° C. Upon reaching 55° C. (after about 2 hours), pressure in reactor increased from initial 10 psig to 55 psig. Reactor was held at 55° C. for 4 hours and pressure further increased to 78 psig. A GC analysis of the reactor organic content after the reaction was completed revealed 64.2 GC Area % of 1234yf, 33.2% GC Area of 244bb, 2.2 GC Area % of 1233xf, and 0.4 GC Area % of unknowns.

The synthesis Example described above is included to illustrate the reaction, and is not a comment on whether the claimed azeotrope or azeotrope-like composition is present in the synthetic procedure.

Example 7—Representative Purification of HCFC-244bb

A composition including HCFC-244bb and water is purified to provide a purified stream of HCFC-244bb.

1000 kg of a mixture including 920.1 kg of HCFC-244bb and 79.9 kg of water is charged to the reboiler of a batch distillation system consisting of a reboiler, multistage rectification section packed with random packing such as IMTP® packing available from Koch-Glitsch and a condenser. The condenser is cooled with flowing chilled water at about 5° C. at the inlet to the condenser. The reboiler has a half-pipe jacket for steam. The reboiler charge could be the organic phase of a mixture of HFC-244bb and water subjected to phase separation where the aqueous phase was decanted off the top.

The batch distillation system is used to distill an overhead stream containing essentially an azeotrope of HCFC-244bb and water, leaving behind in the reboiler substantially HCFC-244bb containing about 0.05 wt % water (see Table 3). The material in the reboiler may be further dried by passing it through a desiccant such as 3A molecular sieves.

TABLE 3

| | Compositions | | |
|---|---|---|---|
| | Reboiler Charge (kg) | Distillate (kg) | Bottoms (kg) |
| HCFC-244bb | 920.1 | 190.0* | 730.1 |
| Water | 79.9 | 79.5 | 0.4 |

Under these conditions, azeotropic composition is 70 wt % HCFC-244bb. Slight excess over the azeotrope is recovered in the overhead.

Although this example shows purification in a batch distillation scheme, it can be adapted to a continuous distillation for purification by those skilled in the art.

Aspects

Aspect 1 is a composition comprising an azeotrope or azeotrope-like composition consisting essentially of effective amounts of 2-chloro-1,1,1,2-tetrafluoropropane (HCFC-244bb) and water.

Aspect 2 is the composition of Aspect 1, wherein the azeotrope or azeotrope-like composition has a boiling point between about 13.5° C. and about 14.5° C. at a pressure of between about 12.5 psia and about 16.5 psia.

Aspect 3 is the composition of Aspect 1 or Aspect 2, wherein the azeotrope or azeotrope-like composition consists essentially of from about 0.05 wt. % to about 92.01 wt. % 2-chloro-1,1,1,2-tetrafluoropropane (HCFC-244bb) and from about 7.99 wt. % to about 99.95 wt. % water.

Aspect 4 is a method of forming an azeotrope or azeotrope-like composition comprising the step of combining 2-chloro-1,1,1,2-tetrafluoropropane (HCFC-244bb) and water to form an azeotrope or azeotrope-like composition consisting essentially of effective amounts of 2-chloro-1,1,1,2-tetrafluoropropane (HCFC-244bb) and water and having a boiling point between about 13.5° C. and about 14.5° C. at a pressure of between about 12.5 psia and about 16.5 psia.

Aspect 5 is the method of Aspect 4, wherein the combining step comprises combining from about 0.05 wt. % to about 99.95 wt. % 2-chloro-1,1,1,2-tetrafluoropropane (HCFC-244bb) and from about 7.99 wt. % to about 99.95 wt. % water.

Aspect 6 is a method of separating impurities from 2-chloro-1,1,1,2-tetrafluoropropane (HCFC-244bb) from a composition which comprises 2-chloro-1,1,1,2-tetrafluoropropane (HCFC-244bb) and at least one impurity, comprising the steps of providing a composition including 2-chloro-1,1,1,2-tetrafluoropropane (HCFC-244bb) and at least one impurity, modifying the relative amounts of 2-chloro-1,1,1,2-tetrafluoropropane (HCFC-244bb) and water, and subjecting the composition to conditions effective to form an azeotrope or azeotrope-like composition consisting essentially of, or consisting of, effective amounts of 2-chloro-1,1,1,2-tetrafluoropropane (HCFC-244bb) and water, and separating the azeotrope or azeotrope-like composition from the composition including 2-chloro-1,1,1,2-tetrafluoropropane (HCFC-244bb).

Aspect 7 is the method of Aspect 6, wherein the step of modifying the relative amounts of 2-chloro-1,1,1,2-tetrafluoropropane (HCFC-244bb) and water comprises adding 2-chloro-1,1,1,2-tetrafluoropropane (HCFC-244bb) to the composition.

Aspect 8 is the method of Aspect 6 or Aspect 7, wherein the step of modifying the relative amounts of 2-chloro-1,1,1,2-tetrafluoropropane (HCFC-244bb) and water comprises adding water to the composition.

Aspect 9 is the method of any of Aspects 6-8, wherein the step of modifying the relative amounts of 2-chloro-1,1,1,2-tetrafluoropropane (HCFC-244bb) and water comprises adding both 2-chloro-1,1,1,2-tetrafluoropropane (HCFC-244bb) and water to the composition.

Aspect 10 is the method of any of Aspects 6-9, wherein the separation step comprises at least one of phase separation, distillation, and fractionation.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances that fall within the scope of the appended claims.

The invention claimed is:

1. A composition comprising a heterogeneous azeotrope or azeotrope-like composition consisting essentially of from about 0.05 wt. % to about 92.01 wt. % 2-chloro-1,1,2-tetrafluoropropane (HCFC-244bb) and from about 7.99 wt. % to about 99.95 wt. % water.

2. The composition of claim 1, wherein the heterogeneous azeotrope or azeotrope-like composition consists essentially of from about 61 wt. % to about 90 wt. % 2-chloro-1,1,1,2-tetrafluoropropane (HCFC-244bb) and from about 10 wt. % to about 39 wt. % water.

3. The composition of claim 1, wherein the heterogeneous azeotrope or azeotrope-like composition has a boiling point between about 13.5° C. and about 14.5° C. at a pressure of between about 12.5 psia and about 16.5 psia.

4. A method of forming a heterogeneous azeotrope or azeotrope-like composition as defined in claim 1, comprising the step of combining 2-chloro-1,1,1,2-tetrafluoropropane (HCFC-244bb) and water to form the azeotrope or azeotrope-like composition.

5. A method of separating 2-chloro-1,1,1,2-tetrafluoropropane (HCFC-244bb) from a primary composition comprising 2-chloro-1,1,1,2-tetrafluoropropane (HCFC-244bb), water, and at least one other substance, comprising the steps of:

subjecting the primary composition to conditions effective to form a heterogeneous azeotrope or azeotrope-like composition consisting essentially of from about 0.05 wt. % to about 92.01 wt. % 2-chloro-1,1,1,2-tetrafluoropropane (HCFC-244bb) and from about 7.99 wt. % to about 99.95 wt. % water; and separating the heterogeneous azeotrope or azeotrope-like composition from the primary composition.

6. The method of claim 5, wherein the at least one other substance comprises 2,3,3,3-tetrafluoropropene (HFO-1234yf), and wherein the separation step comprises at least one of phase separation, distillation, and fractionation.

7. The method of claim 5, further comprising converting at least some of the 2-chloro-1,1,1,2-tetrafluoropropane (HCFC-244bb) present in the heterogeneous azeotrope or azeotrope-like composition into 2,3,3,3-tetrafluoropropene (HFO-1234yf).

8. The method of claim 7, wherein converting at least some of the 2-chloro-1,1,1,2-tetrafluoropropane (HCFC-244bb) into 2,3,3,3-tetrafluoropropene (HFO-1234yf) comprises reacting the 2-chloro-1,1,1,2-tetrafluoropropane (HCFC-244bb) with a base.

9. The method of claim 8, wherein the base is an alkali metal hydroxide.

10. The method of claim 7, wherein converting the 2-chloro-1,1,1,2-tetrafluoropropane (HCFC-244bb) into 2,3,3,3-tetrafluoropropene (HFO-1234yf) occurs in an aqueous environment in the presence of a phase transfer catalyst.

11. The method of claim 7, wherein converting the 2-chloro-1,1,1,2-tetrafluoropropane (HCFC-244bb) into 2,3,3,3-tetrafluoropropene (HFO-1234yf) occurs at a temperature of from about 0° C. to about 100° C.

12. The method of claim 7, wherein the heterogeneous azeotrope or azeotrope-like composition is present in a recycle line that transfers 2-chloro-1,1,1,2-tetrafluoropropane (HCFC-244bb) to the reaction that converts 2-chloro-1,1,1,2-tetrafluoropropane (HCFC-244bb) into 2,3,3,3-tetrafluoropropene (HFO-1234yf).

13. The method of claim 10, wherein the phase transfer catalyst is an ammonium halide.

14. The method of claim 10, wherein the phase transfer catalyst is a trialkylammonium halide or a tetraalkylammonium halide.

15. The method of claim 10, wherein converting the 2-chloro-1,1,1,2-tetrafluoropropane (HCFC-244bb) into 2,3,3,3-tetrafluoropropene (HFO-1234yf) occurs at a temperature of from 20° C. to 90° C.

16. The method of claim 10, wherein converting the 2-chloro-1,1,1,2-tetrafluoropropane (HCFC-244bb) into 2,3,3,3-tetrafluoropropene (HFO-1234yf) occurs at a temperature of from 50° C. to 90° C.

17. The method of claim 7, wherein converting at least some of the 2-chloro-1,1,1,2-tetrafluoropropane (HCFC-244bb) into 2,3,3,3-tetrafluoropropene (HFO-1234yf) comprises reacting the 2-chloro-1,1,1,2-tetrafluoropropane (HCFC-244bb) in a vapor phase dehydrochlorination reaction.

18. The method of claim 7, wherein the vapor phase dehydrochlorination reaction is conducted in the presence of a catalyst.

19. The method of claim 5, wherein the at least one other substance comprises hydrogen fluoride (HF), and wherein the separation step comprises at least one of phase separation, distillation, and fractionation.

* * * * *